United States Patent [19]

Notte et al.

[11] Patent Number: 5,900,519

[45] Date of Patent: * May 4, 1999

[54] CATALYTIC PROCESS FOR THE SELECTIVE ALKYLATION OF POLYCYCLIC AROMATIC COMPOUNDS

[75] Inventors: Patrick Pierre Bernard Notte, Wavre; Georges Marie Joseph Luc Poncelet, Brussels; Marc Joseph Henri Remy, Louvain-La-Neuve; Pierre Fernand Marcel Ghislain Lapdinois, Lobbes; Marina Jeanne Madeleine Van Hoecke, Brussels, all of Belgium

[73] Assignee: Solutia Inc., St. Louis, Mo.

[ * ] Notice: This patent issued on a continued prosecution application filed under 37 CFR 1.53(d), and is subject to the twenty year patent term provisions of 35 U.S.C. 154(a)(2).

[21] Appl. No.: 08/742,555

[22] Filed: Oct. 28, 1996

Related U.S. Application Data

[63] Continuation of application No. 07/922,270, Jul. 30, 1992, abandoned.

[30] Foreign Application Priority Data

Aug. 21, 1991 [EP] European Pat. Off. ............... 91870128

[51] Int. Cl.⁶ ...................................................... C07C 2/66
[52] U.S. Cl. ........................................... 585/446; 585/467
[58] Field of Search ................................. 585/446, 466, 585/467, 475

[56] References Cited

U.S. PATENT DOCUMENTS

| | | | |
|---|---|---|---|
| 3,699,048 | 10/1972 | Krueger, et al. | 252/180 |
| 4,204,953 | 5/1980 | Hodgson et al. | 210/58 |
| 4,447,669 | 5/1984 | Harmon et al. | 585/640 |
| 4,738,940 | 4/1988 | Dufresne et al. | 502/66 |
| 4,795,847 | 1/1989 | Weitkamp et al. | 585/467 |
| 4,891,448 | 1/1990 | Garces et al. | 585/453 |
| 4,950,817 | 8/1990 | Botta et al. | 570/208 |
| 4,950,832 | 8/1990 | Kojima | 585/463 |
| 4,970,338 | 11/1990 | Matsuda et al. | 562/416 |
| 4,982,037 | 1/1991 | Nakamura et al. | 585/467 |
| 5,003,120 | 3/1991 | Newman et al. | 585/323 |
| 5,003,122 | 3/1991 | Fellman et al. | 585/466 |
| 5,004,841 | 4/1991 | Lee et al. | 568/678 |
| 5,026,940 | 6/1991 | Fellmann et al. | 585/467 |
| 5,026,942 | 6/1991 | Fellmann et al. | 585/467 |
| 5,320,779 | 6/1994 | Fivizzani | 252/394 |

FOREIGN PATENT DOCUMENTS

| | | | |
|---|---|---|---|
| 0162733 A2 | 11/1985 | European Pat. Off. | |
| 0234974 A1 | 9/1987 | European Pat. Off. | |
| 0288582 | 2/1988 | European Pat. Off. | C07C 2/66 |
| 0285280 | 5/1988 | European Pat. Off. | C07C 15/14 |
| 0317907 | 5/1989 | European Pat. Off. | C07B 37/02 |
| 0366515 | 2/1990 | European Pat. Off. | C07C 2/66 |
| 0433932 | 6/1991 | European Pat. Off. | C07C 2/66 |
| 0456839 | 11/1991 | European Pat. Off. | C07C 2/70 |
| 2519335 | 7/1983 | France . | |
| 9108181 | 6/1991 | Japan | C07C 2/70 |
| 45246 | 1/1992 | Japan . | |
| 8803523 | 3/1988 | WIPO | C07C 2/66 |
| 9003960 | 4/1990 | WIPO | C07C 2/64 |
| 9003961 | 4/1990 | WIPO | C07C 2/68 |
| 9103443 | 3/1991 | WIPO | C07C 2/68 |

OTHER PUBLICATIONS

Derwent Abstract FR 2 519 335 (WPI Acc No.: 83–730557/198332) ,Jul. 1983.

N.Y.Chen et al., Inorganic Chemistry vol. 15, No. 2, p. 295, (1976); Preparation of Dealuminized Mordenite.

Philipe Bodart et al., Aluminum Siting in Mordenite and Dealumination Mechanism,. Phys. Chem. (1986) 90, 5183–5190.

Jacobs, Peter A; Carboniogenic Activity of Zeolites; Centrum voor Oppervlaktescheikunde en Colloidale Scheikunde, Katholieke Universiteit Leuven, Belgium, Elsevier Scientific Publishing Company—(1977) p. 46.

N.Y. Chen and F.A. Smith Preparation of Dealuminized Mordenite: Inorganic Chemistry, vol. 15, No. 2 (1976) pp. 295–297.

Raatz et al "Comparison Between Small Port and Large Port Mordenites" 1985.

G.S. Lee et al "Shape Selective Alkylation of Polynuclear Aromatics With Mordinite Catalysts: A High Yield Synthesis of 4,4'Diisopropyl–biphenyl" Catalyst Letters 2(1989) pp. 243–248.

Chemical Abstract, vol. 113, No. 15, Oct. 8, 1990 Abstract No. 131709N, p. 603, col. 1.

Japanese Patent Office—Patent Gazette; Patent Publication #Hei 4–5246, Preparation of Alkyl Biphenyls, Jan. 9, 1992.

Chemical Abstract, vol. 105, No. 7, Aug. 18, 1986 Abstract No. 60437U, p. 597, col. 2.

*Primary Examiner*—Walter D. Griffin
*Attorney, Agent, or Firm*—Fitzpatrick, Cella, Harper & Scinto

[57] ABSTRACT

A catalytic process is described for the selective alkylation of a polycyclic aromatic compound comprising reacting the polycyclic aromatic compound with an alkylating agent in the presence of a catalyst to thereby yield the desired alkyl substituted polycyclic aromatic compound with improved selectivity and improved yield. The process is particularly suitable for the selective dialkylation of polycyclic aromatic compounds in the para-, respectively beta-positions. The catalyst is a protonic form of a mordenite having an atomic Si/Al ratio of at least 5:1, comprising additional metal species in a molar ratio metal (in the metal species)/aluminium of at least 0.10 and having a biphenyl sorption of at least 0.05 g biphenyl per g of catalyst.

20 Claims, No Drawings

CATALYTIC PROCESS FOR THE SELECTIVE ALKYLATION OF POLYCYCLIC AROMATIC COMPOUNDS

This application is a continuation of U.S. patent application Ser. No. 07/922,270, filed Jul. 30, 1992, now abandoned, the contents of which are hereby incorporated by reference.

This invention relates to a catalytic process for the selective alkylation of polycyclic aromatic compounds. In particular this invention relates to a catalytic process for the alkylation of polycyclic aromatic compounds yielding improved conversion and increased alkylation selectivity towards para-positions, employing as catalyst a protonic mordenite which furthermore contains additional metal species. The invention also relates to the use of the said catalyst for the selective alkylation of polycyclic aromatic compounds.

Alkylated polycyclic aromatic compounds are of high value to the chemical industry. They are used in various applications, for example as solvents for chromogens in the manufacture of carbonless copying paper and as intermediates which may be converted by oxidation into raw materials for the manufacture of polymers such as liquid crystal polymers and high-performance polyesters. For the latter application, the industry uses large quantities of alkylated, mainly dialkylated, polycyclic aromatic compounds. Most desirable are dialkylated compounds in which the alkyl groups are located in the para-positions, because the said raw materials derived therefrom are suitable for the manufacture of linear polymers.

By para-position(s) are meant herein the 4-position in monocyclic aromatic compounds and equivalent positions, i.e., the position(s) at the extremities of a non-fused polycyclic aromatic compound and at the beta-positions of fused ring systems, such as to provide a product which has the smallest critical diameter. By beta-positions is meant herein the 2, 3, 6 and 7 positions in naphthalene, in biphenylene, in fluorene, in anthracene, or equivalent positions in other fused ring systems. In a similar way is referred herein to para- or linear alkylated isomers or compounds. By ortho- and meta-position is meant herein the 2-, respectively 3-position in monocyclic aromatic compounds, equivalent positions in non-fused polycyclic aromatic compounds and equivalent alpha-positions in fused ring systems, i.e. 1,4,5, 8-positions in naphthalene, biphenylene, fluorene, anthracene and equivalent positions in other fused ring systems. Similarly is referred herein to ortho-, meta- and kinked isomers, i.e. these aromatic compounds in which at least one alkyl group is attached in an ortho-, meta- or equivalent position of the aromatic ring. The latter molecules have larger critical diameters in comparison with the para- or linear alkylated isomers.

To fulfil the industry's needs for dialkylated polycyclic aromatic compounds many manufacturing processes have been developed ranging from alkylation processes using homogeneous Friedel-Crafts-type catalysts such as aluminium trichloride to alkylation processes using heterogeneous catalysts, such as zeolite-type catalysts.

Due to various disadvantages inherent to the use of homogeneous catalyst systems for the alkylation of aromatic compounds, such as e.g. the problems usually encountered with the separation of the reaction product(s) from the reaction mixture, the polluting character of catalyst-derived side products and residues, processes using homogeneous Friedel-Crafts-type catalysts have lost nowadays importance in favour of processes which use a heterogeneous catalyst. In the latter, separation of the catalyst from the reaction mixture is very easy and substantially no catalyst-derived side products or residues are formed. Furthermore unreacted reagents as well as partially alkylated products and undesired position isomers can be easily recycled in the process and converted into desired reaction products. However, a major weakness of alkylation processes of aromatic compounds which use a heterogeneous catalyst is, in general, the moderate selectivity and conversion rate: monoalkylation of monocyclic aromatic compounds proceeds in general satisfactorily; dialkylation of these compounds often shows lowered conversion rates and reduced selectivity. The alkylation, particularly the dialkylation of polycyclic aromatic derivatives, the ones containing fused ring systems as well as the ones containing non-fused ring systems, proceeds in general with poor selectivity and a moderate to poor conversion rate.

The difference in efficiency of the catalytic alkylation between monocyclic and polycyclic aromatic compounds can be explained by the significant difference in molecular dimensions which exists between monocyclic and polycyclic aromatic compounds and by the fact that the alkylation reaction occurs, at least to a major extent, at the inside of the pore channels of the catalyst. Therefore reaction conditions, results and even catalysts suitable for the alkylation of monocyclic aromatic compounds cannot be simply transposed to the alkylation of polycyclic aromatic compounds.

To improve the conversion and/or selectivity of the alkylation of aromatic compounds, particularly in view of the manufacturing of dialkylated polycyclic aromatic compounds in which the alkyl groups are located in the para-positions, various heterogeneous catalysts have been developed. A class of promising heterogeneous catalysts which has been identified comprises zeolite-type catalysts. Furthermore, to remedy catalyst poisoning, a weakness encountered with many zeolite catalysts, various types of zeolite catalysts have been developed the acidity of which has been reduced by introduction of metal species such as metal cations and metal oxides.

Several patents to Mobil Oil, inter alia EP-0.053.423, EP-0.039.536 and U.S. Pat. No. 4.276.437 describe the alkylation and/or transalkylation of monocyclic aromatic derivatives to produce a mixture of dialkyl benzene derivatives in which the 1,4-dialkyl benzene isomer is in excess of its normal thermodynamical equilibrium concentration. In these processes the catalyst is typically a crystalline zeolite catalyst principally of the pentasil zeolites ZSM family, having a silica to alumina ratio of at least 12, a constraint index within the approximate range of 1 to 12, the acidity of which is possibly modified by a metal cation or a metal oxide.

The constraint index is determined by passing continuously a mixture of equal weight of normal hexane and 3-methyl pentane over a sample of the zeolite at atmospheric pressure in standard conditions and assessing by a conventional procedure the remaining amount of the two hydrocarbons.

The constraint index (C.I.) is calculated as follows:

C.I.=log (fraction of hexane remaining)/log (fraction of 3-methyl pentane remaining).

EP-A-0,202752 describes a process for the alkylation of multi-ring aromatic hydrocarbon compounds using a medium pore or large pore zeolite which is preferably at least partly in the protonic form and may contain also magnesium and/or phosphorus compounds. Alkylations of naphthalene and biphenyl carried out using as catalyst zeolite ZSM-5/ZSM-11 and zeolite ZSM-5/ZSM-11 containing magnesium and/or phosphorus compounds showed selectivity towards the 2,6 positions of naphthalene and the 4-, respectively the 4, 4'-positions of biphenyl. The overall yield of desired reaction product (yield being conversion times selectivity both expressed in mole percent) is however low.

U.S. Pat. No. 4,444,989 describes a catalytic process for making para-xylene from toluene and a methylating agent using as catalyst microporous crystalline silica which optionally further contains as promotor arsenic oxide, magnesium oxide, antimony oxide, boron oxide or amorphous silica. The disclosed results show a very good selectivity towards the formation of para-xylene but a poor conversion rate of toluene.

U.S. Pat. No. 4,670,617 describes the use as catalyst in the propylation of toluene of a crystalline silica molecular sieve, essentially free of aluminium and containing zinc atoms in the crystal framework. The para-selectivity obtained is moderate to high, but the percent conversion is mostly low to moderate.

JP 56-133,224 discloses the manufacture of dialkybenzenes by alkylation of a monoalkyl benzene using as catalyst either an acid extracted acidic form of a mordenite optionally modified by exchange of part of the hydrogen cations by non-alkali metal cations, or a non-alkali metal oxide impregnant of an acid extracted acidic form of a mordenite. The examplified iso-propylation of cumene proceeds with good para-selectivity but poor conversion.

JP 58-159,427 discloses a process for the manufacture of dialkylbenzenes by alkylation of benzene or alkylbenzenes in the presence of a protonic form of a mordenite the acidity of which is modified by treatment with caustic soda so as to have an Hammet acidity function (Ho) of less than minus 8.2. The process enables the manufacture of para-dialkylated benzene compounds with good selectivity but with poor to moderate conversion.

JP 56-156,222 describes a method for producing mixtures of monoalkyl biphenyl compounds which are enriched in meta- and para-isomers by alkylation of biphenyl in the presence of a silica-alumina or zeolite catalyst. Selectivity of meta- and para-alkylation is moderate.

EP-Application 91870050.1 describes the use of a protonic form of a dealuminated small pore mordenite having an atomic Si/Al ratio of at least 10:1 as catalyst for the selective alkylation of aromatic hydrocarbon derivatives with improved selectivity control towards para- dialkylated isomers and improved conversion rates. The desirable catalytical activity is obtained in particular if dealumination is carried out on a protonic or ammonium form of the mordenite by consecutively combined hydrothermal and acid treatments.

In spite of the existing processes for the alkylation of aromatic compounds, the industry is still in demand of a process which enables to produce alkylated polycyclic aromatic compounds, particularly para-dialkylated polycyclic aromatic compounds, with a high degree of selectivity and in high yield.

It is an object of this invention to provide a catalytic process for the alkylation of polycyclic aromatic compounds yielding improved conversion and increased selectivity towards alkylation in the para-positions.

It is another object of this invention to use certain mordenites as catalyst in a process for the alkylation of polycyclic aromatic compounds which yields improved conversion and improved selectivity towards para-positions.

It was found that certain mordenites containing additional metal species are suitable catalysts for the selective alkylation in high yields of polycyclic aromatic compounds. This observation forms the basis of the present invention.

In one aspect, the present invention relates to a process for the selective alkylation of a polycyclic aromatic compound by reacting the polycyclic aromatic compound with an alkylating agent in the presence of a mordenite catalyst. The essential catalyst according to the invention is a protonic form of a mordenite having an atomic Si/Al ratio of at least 5:1, comprising additional metal species in a molar ratio metal (in the metal species)/aluminium of at least 0.10 and of which the biphenyl sorption when containing the metal species is at least 0.05 g biphenyl per g of catalyst (dry weight).

In a preferred embodiment the invention relates to a process for the selective para-dialkylation of a polycyclic aromatic compound by reacting the polycyclic aromatic compound with an alkylating agent in the presence of the said mordenite catalyst.

By "aluminium" in the said atomic Si/Al ratio and in the said molar ratio metal/aluminium is meant herein all aluminium present in the mordenite apart from aluminium additionally introduced in the mordenite by cation exchange and/or impregnation.

By "additional metal species" and "metal species" are meant herein any metallic element apart from the above said "aluminium" which may be present in any form or any combination of forms. Such forms include metal cations, elemental metal, and metal in the form of oxide, sulfate and any other metal containing compound. The terms "additional metal species" and "metal species" also include any mixture of any species of two or more metals. Both terms are used herein interchangeably.

Silicon and aluminium levels as well as levels of all other metals present in the metal species of the catalyst indicated herein have been determined by known techniques, in casu Inductively Coupled Plasma Emission Spectroscopy using a Philips PV8490 equipment with an argon plasma operated between 6000 and 11000 degrees Kelvin.

A mordenite is an aluminosilicate which generally has an atomic Si/Al ratio of about 5:1. Its structure and properties are well known in the art and described for example in Zeolite Molecular Sieves, by D. W. Breck (J. Wiley, 1974). The crystalline structure consists in a series of tetraedrons based on $SiO_4$ and $AlO_4$. Their organization results in two types of channels: one defined by eight-membered rings with free apertures of 2.9×5.7 Angstroms and a second one defined by twelve-membered rings with free apertures of 6.7×7 Angstroms along the c-axis. There are two types of mordenites which can be distinguished by their adsorption properties: large pore mordenites, which adsorb molecules like benzene with a kinetic diameter of about 6.6 Angstroms, and small pore mordenites, which only adsorb smaller molecules with a kinetic diameter of about 4.4 Angstroms. The diffusion limitation existing in small pore mordenites may be due to the presence of amorphous material in the channel system, to the nature of the cations, and/or to the presence of crystal stacking defaults in the c-direction of the mordenite.

The aluminosilicate mordenite may further contain small amounts of other elements which may form part of the crystal network, such as e.g. small amounts of iron or germanium.

Large pore mordenites usually appear as spherulites whereas small pore mordenites merely appear as rods.

The characteristics of small pore mordenites are described, for example, by F. Raatz et al. in J. Chem. Soc. Faraday Trans 1, 79, 2299 to 2309 (1983); by P. C. van Geem et al. in J. Phys. Chem, 92, 1585 to 1589, (1988) and by D. W. Breck in Zeolite Molecular Sieves on pages 122 to 125, ( J. Wiley—1974).

In another aspect the invention relates to the use of the said mordenite as catalyst in a process for the selective alkylation, in particular the selective para-dialkylation, of a polycyclic aromatic compound, the process comprising reacting the polycyclic aromatic compound with an alkylating agent in the presence of the said mordenite catalyst.

In a further preferred embodiment the said mordenite catalyst is prepared from a non-dealuminated large pore mordenite.

In another preferred embodiment the said mordenite catalyst is prepared from a dealuminated large pore mordenite.

In still another preferred embodiment the said mordenite catalyst is prepared from a dealuminated small pore mordenite.

The polycyclic aromatic compound suitable for use according to the present invention corresponds to formula (I)

$$Ar^1 (-X-Ar^2)_n-Ar^3 \qquad (I)$$

wherein
- $Ar^1$ may represent a non-substituted or substituted phenyl group or a non-substituted or substituted fused or non-fused polycyclic aromatic hydrocarbon group;
- $Ar^2$ may represent a non-substituted or substituted phenyl group;
- Ar3 may represent a hydrogen atom or a non-substituted or substituted phenyl group;
- X may be absent or represent an oxygen atom, a sulphur atom, a carbonyl group, a sulfonyl group or a $C_1$–$C_4$ alkylene group;
- n may be zero, one or two, provided that, when n is zero and $Ar^1$ is a phenyl group, then $Ar^3$ is different from hydrogen.

The phenyl groups in $Ar^1$, $Ar^2$ and $Ar^3$ and the fused or non-fused polycyclic aromatic hydrocarbon group in $Ar^1$ may be substituted, independently from each other, by one or more substituents selected from a halogen, a hydroxy group, a $C_1$–$C_6$ alkoxy group, a $C_1$–$C_4$ alkoxycarbonyl group, or a $C_1$–$C_{20}$ alkyl group which itself may be substituted by a halogen, a hydroxy, a $C_1$–$C_4$ alkoxy, a carboxy or a $C_1$–$C_4$ alkoxycarbonyl radical; provided that, if $Ar^1$ and/or $Ar^3$ represent a phenyl group or if $Ar^1$ represents a non-fused polycyclic aromatic hydrocarbon, then at least one para-position is unsubstituted, and if $Ar^1$ represents a fused polycyclic aromatic hydrocarbon group, then at least one beta-position is unsubstituted.

A preferred subclass of polycyclic aromatic compounds of formula I embraces the compounds wherein:
- $Ar^1$ represents a non-substituted or substituted phenyl group or a non-substituted or substituted 1,1'-biphenyl group, a para-terphenyl group, a naphthyl group, a fluorenyl group or an anthracenyl group,
- $Ar^2$ represents a non-substituted or substituted phenyl group,
- $Ar^3$ represents a hydrogen atom or a non-substituted phenyl group,
- X may be absent or represent an oxygen atom, a sulphur atom, a carbonyl group, a sulfonyl group or a $C_1$–$C_4$ alkylene group,
- n may be zero, one or two, provided that when n is zero and $Ar^1$ is a phenyl group, then $Ar^3$ is different from hydrogen.

A more preferred subclass of polycyclic aromatic compounds includes the compounds of formula (I) wherein:

- $Ar^1$, $Ar^2$ and $Ar^3$ represent a non-substituted phenyl group, or a phenyl group which optionally can be substituted, independently from each other, by one $C_1$–$C_{20}$ alkyl group, leaving at least a para-position of $Ar^1$ or $Ar^3$ unsubstituted;
- X may be absent or represent an oxygen atom, a sulphur atom, or a $C_1$–$C_4$ alkylene group; and n may be zero, one or two.

Another preferred subclass of polycyclic aromatic derivatives includes the derivatives of formula (I) wherein:
- $Ar^1$ represents a naphthyl, fluorenyl or anthracenyl group,
- $Ar^2$ is a phenyl group, $Ar^3$ represents hydrogen, X is absent, and
- n is zero or one.

Particularly preferred derivatives of formula (I) are, respectively, biphenyl, p-terphenyl, naphthalene, diphenyl ether, 1,4-diphenoxy benzene, mono-($C_1$–$C_{12}$)-alkyl biphenyl, mono-($C_1$–$C_{12}$) alkyl naphthalene.

The most preferred derivatives of formula (I) are, respectively, biphenyl, p-terphenyl, naphthalene, diphenyl ether and 1,4-diphenoxy benzene.

Alkylating agents suitable for use according to the invention comprise C2–C20 alkenes, C2–C20 polyolefins, C4–C7 cycloalkenes, C1–C20 alkanols, C1–C20 alkyl halides and C1–C20 alkyl(monocyclic and polycyclic) aromatic hydrocarbon compounds. Typical alkylating agents are C2–C12 alkenes, C1–C12 alkanols, C1–C12 alkyl halides and C1–C12 alkyl aromatic hydrocarbon compounds, such as, for example, ethylene, propylene, 1-butene, 2-butene, isobutene, 1-pentene, 2-pentene, 1-hexene, 2-hexene, 1-octene, 1-decene, 1-dodecene, methanol, ethanol, 1-propanol, 2-propanol, 1-butanol, 2-butanol, 2-methyl-1 propanol, 2-methyl 2-propanol, 1-pentanol, 1-hexanol, 1-octanol, 1-decanol, 1-dodecanol, and C1–C12 alkyl chloride, C1–C12 alkyl bromide and C1–C12 alkyl iodide such as e.g. methyl chloride, methyl bromide, methyl iodide, ethyl chloride, 1-chloropropane, 2-chloropropane, 2-bromopropane, 1-butyl chloride, 2-pentyl chloride, 2-pentyl bromide, 1-hexyl chloride, 2-hexyl chloride, 2-hexyl bromide, 1-octyl chloride, 1-decyl chloride, 1-dodecyl chloride, mono- and diisopropyl benzenes, and mono- and diisopropyl naphthalenes.

Preferred alkylating agents are C3–C4 alkenes, $C_1$–$C_4$ alkyl halides and C1–C4 alkanol derivatives. The most preferred alkylating agents are propene, 1-propanol, 2-propanol, and isopropyl chloride.

The catalysts according to the invention may be prepared by introduction of desired metal species into a mordenite, preferably into a protonic or ammonium form of the mordenite by one or more techniques well known in the art, preferably by cation exchange, by impregnation or by a combination thereof, but employing a procedure which ensures that the obtained metal species containing catalyst is partly present in a protonic form.

In one embodiment of the invention the catalyst is prepared from a large pore mordenite. The large pore mordenite can be a natural mordenite or a synthetic mordenite, the manufacture of the latter being well known in the art. If the mordenite is not present in an ammonium or protonic form, it may be first transformed into it by exchange with diluted acid or ammonium salts. The protonic form may be obtained from the ammonium exchanged mordenites by calcination. These treatments are carried out by conventional techniques well-known in the art. Synthetic protonic large pore mordenites are commercially available, for example as HSZ-640 from Tosoh, Japan. Typically, the analysis of this mordenite shows an atomic Si/Al ratio of about 9.8:1, a total pore volume of about 0.26 ml/g, a symmetry index of about 1.4 and a ratio of meso plus macro porosity over the total porosity of about 0.3.

The large pore mordenite, preferably in the protonic or ammonium form may be transformed into a metal species containing mordenite according to the invention by conventional methods, as e.g. described hereinafter.

In another preferred embodiment the catalyst according to the invention is prepared starting from a natural or synthetic small pore mordenite zeolite containing as cations alkaline metal, alkaline-earth metal or ammonium ions. Synthetic small pore mordenites can be prepared by techniques well known in the art. The starting small pore mordenite is preferably an alkaline metal containing mordenite, most preferably a sodium containing mordenite, the preparation of which is described, for example, in French Patent 1411753. Such small pore mordenites are commercially available, for example as ZM-060 mordenite from La Grande Paroisse, (France), and have narrowly defined crystallographic properties. This synthetic mordenite has a crystalline structure, as determined by conventional X-ray diffraction, which contains a majority of domains of Cmcm symmetry and which is substantially free of domains of Cmmm symmetry. By the term "which contains a majority" is meant that the crystalline structure is composed of generally more than 90%, preferably more than 95% and most preferably more than 99% of domains of Cmcm symmetry. By the term "substantially free" is meant that no domains of Cmmm symmetry are detectable in the mordenite by conventional X-ray diffraction. This means that the level of possible domains of Cmmm symmetry in the mordenite is less than 0.5%, most preferably less than 0.01%. This starting sodium mordenite has a symmetry index of 0.7 and is present in major part in the form of aggregates composed of rods. The rods have a mean length of about 50000 Angstroms with a hexagonal section of a mean width of about 10000 Angstroms and a mean height of about 3000 Angstroms.

Generally these rods form aggregates with dimensions ranging from about 1 to 1000 microns, typically ranging from about 1 to 100 microns. The aggregate dimensions have been assessed using a Sympatec Laser Particle Analyzer after dispersion of the mordenite in water by use of an ultrasonic bath. X-ray diffraction spectra have been made using a Siemens D-500 equipment and using the K alpha 1 radiation of copper as a source.

The unit cell of this mordenite has the following elementary formula: $Na_7Al_7Si_{40}O_{94}.24H_2O$. The atomic Si/Al ratio is between 4.5 and 6.5, typically close to 6. The sodium level of the dried mordenite is between 4 and 6.5% by weight, typically about 5.3% by weight.

The starting small pore mordenite described above does not adsorb biphenyl in a significant amount. Typically this mordenite has a sorption capacity for biphenyl of about 0.01 to 0.02 g per g of mordenite, calculated on the dried mordenite.

Biphenyl sorption is measured by submitting the mordenite at 200° C. to a helium stream containing 1600 Pa biphenyl until the mordenite is saturated as assessed by flame ionization detection of the biphenyl in the helium stream downstream of the sorption vessel.

In a preferred embodiment the small pore mordenite according to the invention is a metal species containing protonic form of a dealuminated small pore mordenite which is prepared from a said natural or synthetic small pore mordenite by a dealumination treatment followed by introduction of the metal species.

Dealumination of a zeolite is a process leading to a zeolite with a higher atomic Si/Al ratio. It may generally be carried out by isomorphous replacement of the aluminium atoms present in the crystalline network by e.g. silicon atoms, or by extraction of the aluminium atoms without their replacement in the crystalline framework. Isomorphous replacement can for example be carried out by exposing the mordenite to $SiCl_4$ vapors at high temperature. According to the extraction technique aluminium can be extracted from the catalyst framework by treatment with a mineral or organic acid or treatment with a complexing agent. Typically the extraction is carried out on a sodium or ammonium mordenite.

Hydrothermal treatment followed up by acid leaching is another process to dealuminate mordenites which is generally carried out on protonic or ammonium mordenites. Still another way to extract aluminium atoms from the mordenite framework is to conduct, preferably on a protonic or ammonium mordenite, a thermal treatment followed up by acid leaching.

In general dealumination is carried out by subjecting the starting zeolite once or more times to a treatment according to one of the said dealumination techniques, or to a combination of treatments according to the said techniques.

The metal species containing small pore mordenite catalyst according to the invention is preferably prepared by dealumination via one or more combined hydrothermal and acid treatments carried out on the ammonium or protonic form of the mordenite, followed by one or more treatments to introduce the metal species.

Preferably, such catalyst is prepared from a sodium small pore mordenite by a treatment which comprises the following sequential steps:

(a)—exchange of the sodium ions by ammonium ions or protons, (b)—thermal treatment in the presence of steam (referred to hereafter interchangeably as "steaming" or "hydrothermal" treatment), (c)—treatment with an aqueous acid solution, (d)—introduction of one or more desired metal species by one or more cation exchange or impregnation treatments or a combination thereof, according to known techniques. When the metal species are introduced via impregnation, the impregnation procedure is usually followed by a calcination; if the metal species are introduced merely via cation-exchange, the calcination treatment is optional.

Typically, the catalyst is prepared as follows:

(a)—sodium ions in the starting mordenite are exchanged by ammonium ions by treatment of the mordenite with an aqueous solution of an ionizable ammonium salt, preferably ammonium nitrate or ammonium acetate, of a molarity generally superior to 0.5 at a temperature generally between about 20° C. and about 150° C. Optionally this cation exchange may be repeated in combination or not with an intermediate wash with demineralised water. Optionally sodium ions extraction can be carried out by treatment of the starting mordenite with a diluted mineral or organic acid. The remaining sodium content, calculated on the dried mordenite, is preferably less than 0.5%, typically less than 0.1%.

(b)—hydrothermal treatment is carried out by heating the ammonium mordenite or protonic mordenite obtained in step (a) for at least 10 minutes at a temperature generally between about 300° C. and about 900° C. in the presence of an atmosphere containing at least about 1% steam. (% is indicated as weight percent). Preferably the mordenite is treated at a temperature between 400° C. and 800° C. for at least 20 minutes in an atmosphere containing at least about 5% steam. The treatment can also be carried out by the so-called self-steaming technique which comprises calcination of the mordenite in a confined atmosphere, as well as by any other convenient technique known in the art. The atmosphere generally comprises, apart from steam, a conventional gas or gas mixture the components of which do not have any poisoning or undesirable effect on the mordenite. Suitable gases and gas mixtures are, for example, nitrogen, helium, air and components of air. During the hydrothermal treatment ammonium ions are decomposed to thereby yield a protonic (acidic) form of the mordenite.

(c)—the steamed mordenite from step (b) is then subjected to an acid treatment which comprises contacting the mordenite with an aqueous acid solution, preferably with an aqueous solution of a mineral acid. Preferably this treatment is done by stirring the mordenite in a solution of a strong mineral acid, generally of a normality between about 0.1 N and 12 N, for at least 10 minutes at a temperature between about 20° C. and about 150° C., and more preferably between about 80° C. and 150° C. Before subsequent drying, typically carried out between about 80° C. and about 150° C., the mordenite may be washed once or several times with an aqueous acid solution and/or demineralised water. Preferably the last wash is carried out with demineralised water.

In order to reach the desired degree of dealumination, the thermal treatment in the presence of steam followed up by an acid treatment may be repeated once or several times. Optionally also the acid treatment may be repeated once or several times either with the same acid, at the same or at a different molarity, or with a different acid. Optionally the last acid treatment may be followed up, preferably after a wash with demineralised water, by a thermal treatment in the absence of added steam typically carried out at a temperature comprised between about 400° C. and about 700° C., according to conventional calcination techniques.

As a result of the hydrothermal treatment aluminium atoms are expelled from the crystalline framework of the catalyst and generally deposited in the porous system. During the subsequent acid treatment most of the aluminium species are dissolved and removed from the catalyst. By the combined hydrothermal and acid treatments the amount of aluminium species removed is generally more than 50% of the total initial aluminium content, typically more than 80%, more preferably more than 90%. The extent of the aluminium species removal can be controlled by the dealumination conditions. These required conditions can be determined by the skilled person by routine experiments. This dealumination treatment increases the atomic Si/Al ratio from its typical original value, being close to 5:1, to an atomic ratio Si/Al of at least 10:1. The dealuminated small pore mordenites for use according to the invention generally have an atomic Si/Al ratio between 10:1 and 500:1, preferably between 30:1 and 200:1, more preferably between 60:1 and 150:1.

It is to be understood that the atomic Si/Al ratio is an overall ratio based on the total amounts of silicon and aluminium in the mordenite (framework plus extra-framework apart from aluminium additionally introduced in the mordenite), and that the atomic ratio Si/Al of the crystalline matrix (framework) may differ significantly and reach higher ratios.

During the dealumination process according to the above described combined hydrothermal and acid treatments the porosity of the small pore mordenite catalyst is significantly modified. After removal of about 20% of the aluminium atoms from the crystalline framework by the combined steaming and acid treatments, the porous system is unblocked and larger molecules like e.g biphenyl can be sorbed in the porous system of the catalyst.

The unblocking of the porous system, allowing free diffusion of molecules of a kinetic diameter of about 6.6 Angstroms such as biphenyl, is a sign of the modifications which occur to the porous system.

The porous system of small pore mordenites generally comprises microporous (radius from about 3 to 15 Angstroms), mesoporous (radius from about 15 to 1000 Angstroms) and macroporous (radius above 1000 Angstroms) components.

By the unblocking, new pores are also created as shown by the increase of the mesoporous and macroporous volumes after the combined treatment of the starting sodium small pore mordenite. Typically biphenyl adsorption will have increased as a result of the combined hydrothermal and acid treatments from about 0.016 g per g of mordenite up to between 0.05 and 0.12 g per g of mordenite, calculated on the dried mordenite. The porous volumes can be calculated by methods known in the art and described for example by S. Lowell in Introduction to Powder Surface Area (J. Wiley, 1979).

The characteristics of typical protonic dealuminated small pore mordenites prepared through the above described procedure of steps (a) to (c) are as follows:

an acidic form, i.e. a form wherein substantially all cations are protons, an atomic Si/Al ratio from about 10:1 to about 200:1, a symmetry index from about 0.7 to about 2.6, a biphenyl sorption capacity from about 0.05 to about 0.12 g per g of catalyst, calculated on a dried basis, a ratio of mesoporous plus macroporous volumes to total porous volume comprised between 0.2 and 0.5, a crystalline structure which is a matrix of Cmcm symmetry substantially free of Cmmm symmetry, appearance in the form of aggregates composed of rods.

The symmetry index has been obtained from the X-ray diffraction spectrum of the mordenite zeolite. It is defined as the sum of the peak height of the (111) and (241) reflections divided by the peak height of the (350) reflection. It is typically between 0.5 and 0.8 for the starting small pore mordenite and is typically comprised between 0.7 and 2.6 after the above dealumination treatment.

(d)—Then one or more desired metal species are introduced to a defined extent into the protonic form of the dealuminated small pore mordenite obtained from step (c) in accordance with known techniques, e.g. as described hereafter.

In another preferred embodiment the mordenite catalyst according to the invention is prepared from a dealuminated large pore mordenite. Starting from a natural or synthetic large pore mordenite dealumination may be carried out by known techniques, preferably by combined hydrothermal and acid leaching treatments, similarly to the ones described above in steps (a) to (c) for the preparation of a protonic dealuminated small pore mordenite. Dealuminated large pore mordenites according to the invention have an atomic Si/Al ratio of at least 10:1, generally between 20:1 and 500:1, typically between 30:1 and 200:1, preferably between 60:1 and 150:1.Then in a next step one or more metal species are introduced to a defined extent into the protonic form of the dealuminated large pore mordenite by known techniques, e.g. as described hereafter.

The techniques for the introduction of additional metal species into a mordenite catalyst in order to prepare a catalyst according to the invention are well known in the art. In general, metal species are introduced in a mordenite by impregnation or by ion-exchange or by a combination thereof. These techniques are similar for the introduction of metal species into non-dealuminated large pore mordenites, dealuminated large pore mordenites, and dealuminated small pore mordenites. Typical procedures are described hereafter.

In a typical impregnation procedure, a protonic or ammonium form of the mordenite is contacted with a solution of a compound of the metal to be introduced. The compound may be an organic or inorganic metal compound. The solution has a concentration, depending on the solubility of the metal compound, generally between 0.1 g/l and 150 g/l. The contact time may vary from a few minutes to several hours and contacting is carried out, usually under stirring, at ambient or elevated temperature. A preferred solvent is water and the metal compound may be present in the solution in ionised or non-ionised form. Other preferred solvents comprise, for example, methanol, dimethyl sulfoxide, N-methyl pyrrolidone, aromatic, aliphatic and aliphatic-aromatic hydrocarbons, and mixtures of any of these solvents, for example a mixture water-methanol. After contacting the mordenite with the metal compound, the solvent is evaporated. Then the obtained mordenite is usually calcined at a temperature which is in general comprised between about 300° C. and 900° C. In the calcination step possibly present ammonium cations are decomposed into protons, and organic and certain inorganic metal compounds are, depending on the nature of the anion, decomposed into the corresponding metal oxides or other metal species. Certain other inorganic salts, for example sulfates, are not decomposed during the calcination step and the metal species will remain in the form of that metal salt in the protonic mordenite.

If the metal compound is ionised in the solution which is used for impregnation, part of the metal species may become introduced into the mordenite in the form of metal cations.

Ion-exchange is a conventional technique well known in the art, by which a cation present in a catalyst, in casu a mordenite, is substituted by another cation by treatment of the mordenite with the desired cation, the latter being present as an aqueous solution of an ionisable salt of the desired metal, the acid rest of which may be organic or inorganic. A typical ion-exchange in a mordenite is the substitution of sodium ions by ammonium ions, by protons or directly by other metal cations, as well as the replacement of protons by cations of one or more metals. After the ion-exchange treatment the mordenite is usually washed with water to remove adsorbed metal salt, commonly followed by a drying step and optionally by a calcination step.

Preferably the ion-exchange treatment of the non-dealuminated large pore, dealuminated large pore and dealuminated small pore mordenites is carried out by stirring the protonic or ammonium mordenite in an aqueous solution of the desired salt, preferably a nitrate, chloride or acetate, having a concentration depending on the solubility of the salt generally between 0.1 g/l and 150 g/l, If necessary the pH of the solution may be adjusted in order to avoid hydrolysis and/or precipitation of hydrolysis products. Stirring is carried out at a temperature between about 20° C. and 150° C., if needed in a closed system in order to reach the desired temperature, for a period ranging from about a few minutes to several hours. To improve intimate contact of the catalyst with the metal salt solution, the catalyst may optionally be degassed by bringing it in a container under vacuum prior to contacting it with the aqueous solution. After treatment the mordenite is separated from the solution by conventional techniques, e.g. centrifugation or filtration, and washed with deionised water to remove the excess of metal salt. To avoid the formation of undesired hydrolysis products the pH of the water may be adjusted by addition of acid e.g. nitric acid, acetic acid, hydrochloric acid.

Commonly the cation exchange treatment is followed by drying of the mordenite at a temperature between about 80° C. and 150° C. Optionally the ion-exchanged mordenite may be further calcined in a known manner, for example, by heating between about 300° C. and 900° C. in an atmosphere the components of which do not have any poisoning or undesirable effect on the ion-exchanged mordenite.

An alternative procedure for the preparation of a metal species containing non-dealuminated large pore mordenite catalyst according to the invention consists in an ion-exchange treatment of a natural or synthetic large pore mordenite, which in general is an alkali metal mordenite, usually a sodium mordenite, either with an aqueous solution containing an ammonium salt and a desired ionisable metal salt or with an aqueous solution containing an acid and a desired metal salt. By this treatment the metal cations originally present in the mordenite are completely or partly exchanged by the desired metal cations and protons or ammonium ions. If ammonium ions are introduced, the ion-exchange procedure is followed by a calcination step during which ammonium ions are decomposed to yield a protonic form of the mordenite catalyst.

Another alternative procedure for the preparation of an alkali metal species containing non-dealuminated large pore mordenite catalyst according to the invention consists in the treatment of a natural or synthetic large pore mordenite, which is in general an alkali metal mordenite, either with an inorganic or organic acid or aqueous solution of such acid, or with an aqueous solution of an ammonium salt (this treatment being followed by a calcination), so as to exchange part of the alkali metal cations by protons.

Metal species of two or more metals may be introduced into the mordenite, either in one operation—through cation exchange as well as through impregnation—using a solution containing a mixture of selected metal compounds which contains the metal compounds in an appropriate molar ratio, or in two or more consecutive operations using each time a solution of one of the selected metal compounds. Optionally, different metal species may be introduced by a combination of cation exchange and impregnation treatments.

The amount of metal species introduced into the mordenite may be controlled by the ion-exchange or impregnation conditions, in particular by the amount of metal compound charged to the mordenite in the impregnation step or used in the ion-exchange procedure. The conditions to prepare a mordenite with a desired molar ratio metal/aluminium can be determined by the skilled person by known methods and/or routine experiments.

The extent of metal species in the mordenite is expressed as molar ratio metal (from the metal species)/aluminium. The number of moles of "aluminium" and of "metal" in the metal species are calculated from the weights of the metal species and "aluminium" present in the mordenite as assessed by the ICAP method. The meaning of the terms "aluminium" and "metal species" have been defined herein before. The ICAP method (Inductively Coupled Argon Plasma emission spectroscopy) is a conventional method well known to the skilled person.

The extent of exchange of protons from a protonic mordenite by metal cations can be controlled by the exchange conditions. The most important parameter is the ratio "r" being the atomic ratio of the metal cations in solution to the aluminium atoms in the catalyst, and in case of a mixture of metal cations the relative molar ratio of the metal salts and their respective ratio "r". The conditions to obtain a desired extent of cation exchange, and thus a desired molar ratio metal (from metal species)/aluminium, can be easily determined by a skilled person on the basis of routine experiments.

The metal species in the mordenite catalysts according to the present invention may include any metal species or mixture of species of two or more metals. It may, for example, be a metal species of a metal from group 1 of the periodic system of elements, i.e. an alkali metal such as e.g. lithium, sodium, potassium, rubidium, cesium; from group 2, i.e. an alkaline-earth metal, such as e.g. beryllium, magnesium, calcium, strontium, barium; from group 3, such as, e.g. lanthanum; from group 4, such as e.g. titanium, zirconium; from group 5, such as e.g. vanadium, niobium; from group 6, such as e.g. chromium, molybdenum, tungsten; from group 7, such as e.g. manganese; from group 8, such as e.g. iron; from group 9, such as e.g. cobalt; from group 10, such as e.g. nickel, palladium, platinum; from group 11, such as e.g. copper, silver, gold; from group 12, such as e.g. zinc, cadmium, mercury; from group 13, such as e.g. aluminium, gallium, indium, thallium; from group 14, such as e.g. germanium, tin, lead; from group 15 such as e.g. arsenic, antimony, bismuth; from group 16 such as selenium, tellurium.

Preferred ones are metal species from group 1, group 2 or group 12. More preferred metal species are lithium, magnesium, calcium or zinc species. Further preferred metal species are cations from lithium, magnesium, calcium and zinc.

The metal species containing mordenites suitable for use according to the present invention comprise metal species to such extent that the molar ratio metal (in the metal species)/aluminium is at least 0.10. By molar ratio metal/aluminium is meant herein the ratio of the total amount (in moles) of additional metal from all metal species present (i.e. from different metallic elements as well as from different species of one metallic element) on the moles of aluminium. Typically the ratio is comprised between 0.10 and 0.85, preferably between 0.20 and 0.70.

Typical catalysts according to the invention are for example a cation-exchanged large pore mordenite, a cation-exchanged dealuminated large pore mordenite and a cation-exchanged dealuminated small pore mordenite, containing lithium, calcium, magnesium or zinc metal species at a molar ratio metal/aluminium from 0.20 to 0.70.

Preferred catalysts according to the invention are cation-exchanged dealuminated small pore mordenites, more preferably the ones containing cations from a metal of group 1, group 2 or group 12. Highly preferred are those mordenites which contain lithium, calcium, magnesium or zinc cations at a molar ratio metal/aluminium from 0.20 to 0.70.

Optionally the sodium, ammonium or proton mordenite before or after the steaming treatment, the acid treatment or the cation exchange treatment may be reduced in size using methods known in the art like e.g. crossed air jet milling. The dimensions of size reduced catalysts generally range from about 0.1 to about 1000 microns, and typically from about 0.1 to about 100 microns. Most preferred sizes range from 0.1 to 10 microns.

The mordenite catalysts according to the invention may be used optionally in combination with a suitable support and/or binder known in the art, in any suitable form, for example in the form of e.g. powder, extrudates, pellets, tablets, granules, spheres, and the like. Such support and binder materials may be inert or may have an intrinsic catalytic activity which is compatible with the desired catalytic activity of the mordenite catalyst according to the invention. Examples of such materials are e.g. oxides like alumina, silica, magnesia and silica-alumina; charcoal, kieselguhr, and various clays. The desired form of the catalyst for use in the alkylation process of the invention may be prepared according to techniques which are well known in the art.

In the alkylation process according to the invention virtually any weight ratio of catalyst to aromatic compound can be used, but practically it is limited by the conversion rate which may not become unacceptably slow. The weight ratio catalyst:aromatic compound is generally kept between about 1:1000 and 1:5, preferably between 1:500 and 1:5, more preferably between 1:100 and 1:10, most preferably about 5:100.

The ratio of alkylating agent:aromatic compound may vary according to the number of alkyl groups which are to be grafted on the aromatic hydrocarbon, the nature of the alkylating agent as well as of the aromatic compound, the catalyst and the reaction conditions such as e.g. temperature, pressure, reaction time and type of reactor. In general, however, the mole ratio of alkylating agent:aromatic compound is kept between 0.5 and 5 per alkyl group to be grafted on the aromatic hydrocarbon, typically between 0.7 and 2, and preferably about 1:1.

The alkylation process according to the invention can be carried out in any batch-type or continuous-type alkylation reactor known in the art, such as for example a fixed bed, slurry bed or fluidized bed reactor, a countercurrent reactor and the like. The alkylation can be carried out with the alkylating agent and/or the aromatic compound in the liquid and/or gas phase, or the aromatic compound or alkylating agent can act as a solvent for the other, or optionally a solvent which remains inert under the reaction conditions can be added. Furthermore the aromatic compound can be brought in contact with the required amount of alkylating agent, or vice versa, at once at the beginning of the reaction, or gradually as the reaction proceeds.

The optimum reaction temperature and pressure depend on the other reaction conditions, e.g. on the type of mordenite, the nature of the metal cations and extent of exchange, the nature of the aromatic compound and the alkylating agent, as well as on the nature of the desired reaction product. Typically the reaction temperature is kept between about 100° C. and about 400° C., preferably between about 150° C. and about 300° C.

The alkylation process can generally be carried out at a pressure ranging from about 1 kPa to about 4000 kPa, typically between about 10 kPa and 1000 kPa, preferably between about 10 kPa and 500 kPa.

The optimum time during which the aromatic compound and the alkylating agent are brought in contact in the presence of the catalyst depends largely on the nature of the aromatic compound, the alkylating agent, the catalyst, the reactor type, and the other reaction conditions. The reaction time may vary from a few seconds to a few hours.

The process according to the invention may yield a mixture of alkylated polycyclic aromatic compounds of various isomers of which the alkylated isomer distribution can be controlled and tuned towards higher levels of the desired para- or linear isomers by selection of the appropriate reaction conditions, in particular the most appropriate catalyst.

For a given aromatic compound the appropriate reaction conditions for optimal production of a selected alkylated isomer or isomer mixture can be defined by the skilled person on the basis of a reasonable amount of routine experiments according to standard techniques of the art. Selection may be made, for example, by comparative evaluation of the evolution of the composition of the reaction products (e.g. by gas chromatography (GC) or GC-mass spectrometry analysis) which are obtained in test runs when one or more reaction parameters are varied.

Alkylation of an aromatic hydrocarbon to a selected isomer or mixture of isomers will, for the purpose of this invention, be qualified by the conversion of the starting aromatic compound, the selectivity towards the desired alkylated isomer and by the yield of such isomer as obtained in the crude alkylation product. Conversion refers to the mole percentage of the starting aromatic compound which has been converted in the alkylation reaction. Selectivity to a given alkylated isomer is the mole percentage of the starting aromatic compound which has been converted into that desired isomer. Selectivity can also be expressed based on a product family, e.g as mole percentage of a particular dialkylated isomer on the total amount of dialkylated isomers formed.

The yield in any particular isomer in the crude alkylated aromatic derivative represents the numerical product of conversion times selectivity.

The following examples are given to illustrate the catalysts, their use and the process according to the present invention, and should not be construed as limiting its scope. All percentages, unless otherwise stated, are expressed in mole percent. Unless otherwise stated the term "added pressure" means the pressure of alkylating agent which is superimposed at the onset of the reaction to the pressure of the reaction mixture at the set reaction temperature. The value of the "added pressure" is maintained throughout the duration of the reaction.

The starting mordenites are a small pore sodium or ammonium mordenite produced, respectively, as ZM-060 and ZM-101 by La Grande Paroisse, France, and protonic large pore mordenites HSZ-640, produced by Tosoh, Japan; CBV 20 A produced by Conteka, The Netherlands, and a mordenite supplied by PQ Corporation, USA.

Comparative examples are also included.

In examples 1 to 17 and in Tables 1 to 11 are indicated the quantity "A" in g of the metal salt used for the exchange, the ratio "r" (i.e. the atomic ratio of the metal cations in solution to the Al atoms in the catalyst) and the amount of metal species in the mordenite, expressed in molar ratio metal/aluminium (indicated hereafter as "M/Al").

Examples 18 to 29 and tables 12 to 27 relate to alkylation procedures and results obtained using catalyst samples described hereafter. In the tables the heading of the columns refer to the following:

"catalyst sample" (number) corresponds to the catalyst sample (number) described in Examples 1 to 17 and in Tables 1 to 11;

"Conv. %" refers to the conversion in mole percent of the starting polycyclic aromatic compound;

"m,p'-yield" and "p,p'-yield" indicate the yield (conversion times selectivity) expressed in mole percent of meta,para'-isomer and para,para'-isomer, respectively;

Di/Conv. indicates the mole ratio of dialkylated isomers formed on the starting polycyclic aromatic compound converted, and expressed in percent;

p,p'-Sel and p,p"-Sel indicate the selectivity in mole percent towards the para,para'-isomer and para,para"-isomer, respectively;

"p-Sel" indicates the selectivity in mole percent towards para-isomers and is the sum of the selectivities towards the p-, and p,p'-isomers;

"2-Sel" indicates the selectivity in mole percent towards the 2-isomers and is the sum of the selectivities towards the 2-, and 2,6-isomers.

p,p'-/Di and 2,6-/Di respectively indicate in mole percent the percentages of the para,para'-isomer, respectively 2,6-isomer in the corresponding family of dialkylated polycyclic aromatic compounds obtained. Analysis of the reaction products are carried out by gas chromatograpy on the crude reaction mixture.

EXAMPLE 1

Preparation of Dealuminated Small Pore Mordenite Catalyst

ZM-060 small pore sodium mordenite is converted to the ammonium form by treatment with an aqueous solution of ammonium nitrate as follows: 400 g of the sodium mordenite are contacted with 1 liter of an aqueous solution containing 100 g of ammonium nitrate. The mixture is stirred at 60° C. for 4 hours. The ammonium mordenite formed is recovered by filtration and washed several times with demineralised water. The ammonium mordenite is subjected to a hydrothermal treatment at atmospheric pressure in a horizontal furnace swept by an air current at a rate of 250 Nliters per hour. The temperature is increased gradually to 680° C. at a rate of 150° C. per hour. Steam is introduced in the air from about 300° C. The steam level is adjusted by means of a saturator. Water flow is close to 80 g per hour. After a period of 5 hours at 680° C. under these conditions the furnace heating is turned off and at 300° C. the steam flow is stopped. The mordenite is then treated at 90° C. with a 6 N aqueous nitric acid solution for 3 hours under vigorous stirring. The catalyst is separated by filtration, washed with deionized water at 70° C. and finally dried under air/vacuum at 150° C. for 10 hours. The analysis of the catalyst gives the following results: an atomic Si/Al ratio of 80:1; a total pore volume of 0.328 ml/g ; a symmetry index of 1.68; a ratio of meso plus macro porosity over the total porosity of 0.33. This catalyst is later referred as sample 1 (comparative sample).

EXAMPLE 2

General Procedure for the Preparation of Alkaline Cation Exchanged Mordenite Catalysts 30 g of sample 1 catalyst are added to a solution of "A" g of an alkaline metal salt in 150 ml of demineralized water. The quantity of the alkaline metal salt added to the solution is calculated such as to have an atomic ratio of the alkaline cations in solution to the Al atoms in the catalyst equal to "r". The mixture is heated at 80° C. and maintained at this temperature for 16 hours under vigorous stirring. The exchanged mordenite is recovered by filtration, washed with demineralized water till free of excess salt, dried in air at 110° C. and then heated at 600° C. in air for 2 hours.

Table 1 lists various alkaline cation exchanged dealuminated small pore mordenite catalysts (samples 2 to 17) prepared by the above general procedure of example 2.

TABLE 1

Alkaline cation exchanged mordenite catalysts

| Sample No | Metal | Salt | Weight of salt (A in g) | ratio r | M/Al |
|---|---|---|---|---|---|
| 2 | Lithium | Acetate.2H2O | 0.13 | 0.25 | 0.11 |
| 3 | Lithium | Acetate.2H2O | 0.27 | 0.50 | 0.28 |
| 4 | Lithium | Acetate.2H2O | 0.54 | 1.00 | 0.50 |
| 5 | Sodium | Acetate.3H2O | 0.18 | 0.25 | 0.21 |
| 6 | Sodium | Acetate.3H2O | 0.37 | 0.50 | 0.36 |
| 7 | Sodium | Acetate.3H2O | 0.73 | 1.00 | 0.57 |
| 8 | Sodium | Acetate.3H2O | 1.47 | 2.00 | 0.66 |
| 9 | Potassium | Acetate | 0.13 | 0.25 | 0.18 |
| 10 | Potassium | Acetate | 0.26 | 0.50 | 0.31 |
| 11 | Potassium | Acetate | 0.53 | 1.00 | 0.45 |
| 12 | Rubidium | Carbonate | 0.31 | 0.25 | 0.40 |
| 13 | Rubidium | Carbonate | 0.62 | 0.50 | 0.72 |
| 14 (a) | Rubidium | Carbonate | 1.25 | 1.00 | 1.06 |
| 15 | Cesium | Carbonate | 0.44 | 0.25 | 0.46 |
| 16 (a) | Cesium | Carbonate | 0.88 | 0.50 | 0.89 |
| 17 (a) | Cesium | Carbonate | 1.76 | 1.00 | 1.09 |

(a) : comparative sample : the biphenyl sorption of samples 12,13,14,15,16 and 17 is respectively 0.08; 0.075; 0.018; 0.08; 0.045; and 0.02 g biphenyl per g catalyst.

EXAMPLE 3

Preparation of Alkaline-earth Cation Exchanged Mordenite Catalysts 30 g of sample 1 catalyst are added to a solution of "A" g of an alkaline-earth metal salt in 150 ml of water. The quantity of alkaline-earth metal salt added to the solution is calculated such as to have an atomic ratio of the alkaline-earth cations in solution to the Al atoms present in the catalyst equal to "r". The mixture is heated at 80° C. and maintained at this temperature for 16 hours under vigorous stirring. The exchanged mordenite is recovered by filtration, washed with demineralized water till free of excess salt, dried in air at 110° C. and then heated at 600° C. in air for 2 hours.

Table 2 lists various alkaline-earth cation exchanged dealuminated small pore mordenite catalysts (samples 18 to 34) prepared by the above general procedure of example 3.

TABLE 2

Alkaline-earth cation exchanged mordenite catalysts

| Sample No | Metal | Salt | Weight of salt (A in g) | ratio r | M/Al |
|---|---|---|---|---|---|
| 18 | Beryllium | Sulfate.2H2O | 0.95 | 1.00 | 0.27 |
| 19 | Beryllium | Sulfate.2H2O | 1.90 | 2.00 | 0.27 |
| 20 | Beryllium | Sulfate.2H2O | 3.80 | 4.00 | 0.33 |
| 21 | Magnesium | Acetate.4H2O | 0.28 | 0.25 | 0.2 |
| 22 | Magnesium | Acetate.4H2O | 0.56 | 0.50 | 0.3 |
| 23 | Magnesium | Acetate.4H2O | 1.12 | 1.00 | 0.35 |
| 24 | Calcium | Acetate | 0.21 | 0.25 | 0.18 |
| 25 | Calcium | Acetate | 0.43 | 0.50 | 0.35 |
| 26 | Calcium | Acetate | 0.86 | 1.00 | 0.38 |
| 27 | Calcium | Acetate | 0.86 | 1.00 | 0.37 |
| 28 | Calcium | Acetate | 0.86 | 1.00 | 0.38 |
| 29 | Strontium | Nitrate | 1.15 | 1.00 | 0.14 |
| 30 | Strontium | Nitrate | 3.45 | 3.00 | 0.19 |
| 31 | Strontium | Acetate | 1.11 | 1.00 | 0.33 |
| 32 | Barium | Acetate | 0.36 | 0.25 | 0.18 |
| 33 | Barium | Acetate | 0.71 | 0.50 | 0.29 |
| 34 | Barium | Acetate | 1.42 | 1.00 | 0.33 |

Samples 26, 27 and 28 are indicative of the reproductivity of the cation exchange. The biphenyl sorption of samples 24, 32 and 33 is respectively 0.069; 0.08 and 0.072 g biphenyl per g catalyst.

EXAMPLE 4

Preparation of Dealuminated Small Pore Mordenite Catalyst

ZM-060 small pore sodium mordenite is treated with ammonium nitrate as in example 1 to exchange the sodium by ammonium cations. The catalyst is dealuminated by thermal treatment carried out in the presence of steam as in example 1. This treatment is carried out at 620° C. for 5 hours. After cooling the catalyst is treated at 90° C. with 6 N aqueous nitric acid under vigorous stirring for 3 hours. The catalyst is separated by filtration, washed with deionized water at 70° C., and finally dried at 150° C. for 10 hours. Analysis of the catalyst gives the following results: atomic Si/Al ratio of 50:1; a symmetry index of 1.85; a total pore volume of 0.32 ml/g; a ratio meso plus macro porosity over the total porosity of 0.42. This catalyst is later referred as sample 35 (comparative sample).

EXAMPLE 5

Preparation of Calcium Cation Exchanged Dealuminated Small Pore Mordenite Catalysts 30 g of sample 35 catalyst are added to a solution of "A" g of calcium acetate in 150 ml of demineralized water. The quantity of calcium acetate added to the solution is calculated such as to have an atomic ratio of the calcium ions in solution to the Al atoms in the catalyst equal to "r". The mixture is heated at 80° C. and maintained at this temperature for 16 hours under vigorous stirring. The exchanged mordenite is recovered by filtration, washed with demineralized water till free of excess salt dried in air at 110° C. and then heated at 600° C. in air for 2 hours.

Table 3 lists some calcium cation exchanged dealuminated small pore mordenite catalysts (samples 36 to 37) prepared by the above method of example 5.

TABLE 3

Calcium cation exchanged mordenite catalysts.

| Sample No | Weight of calcium acetate (A in g) | ratio r | M/Al |
|---|---|---|---|
| 36 | 2.00 | 1.00 | 0.31 |
| 37 | 4.00 | 2.00 | 0.38 |

EXAMPLE 6

Preparation of Dealuminated Small Pore Mordenite Catalyst

ZM-060 small pore sodium mordenite is treated with ammonium nitrate as in example 1 to exchange the sodium by ammonium cations. The catalyst is dealuminated by thermal treatment carried out in the presence of steam as in example 1; this treatment is carried out at 560° C. for 5 hours. After cooling the catalyst is treated at 90° C. with 1 N aqueous nitric acid under vigorous stirring for 3 hours. The catalyst is separated by filtration, washed with deionized water at 70° C. and finally dried at 150° C. for 10 hours. Analysis of the catalyst gives the following results: atomic Si/Al ratio of 11:1; a symmetry index of 1.09; a total pore volume of 0.265 ml/g; a ratio meso plus macro porosity over the total porosity of 0.24. This catalyst is later referred as sample 39 (comparative sample). R-839

EXAMPLE 7

Preparation of Calcium Cation Exchanged Cealuminated Mordenite Catalysts 30 g of sample 39 catalyst are added to a solution of "A" g of calcium acetate in 150 ml of water. The quantity of calcium acetate added to the solution is calculated such as to have an atomic ratio of the calcium ions in solution to the Al atoms present in the catalyst equal to "r". The mixture is heated at 80° C. and maintained at this temperature for 16 hours under vigorous stirring. The calcium exchanged mordenite is recovered by filtration, washed with demineralized water till free of excess salt, dried in air at 110° C. and then heated at 600° C. in air for 2 hours.

Table 4 lists some calcium cation exchanged dealuminated small pore mordenite catalysts (samples 40 and 41) prepared by the above method of example 7.

TABLE 4

Calcium cation exchanged mordenite catalysts.

| Sample No | Weight of calcium acetate (A in g) | ratio r | M/Al |
|---|---|---|---|
| 40 | 7.20 | 1.00 | 0.19 |
| 41 | 14.20 | 2.00 | 0.25 |

EXAMPLE 8

Preparation of Calcium Cation Exchanged Large Pore Mordenite Catalyst

Analysis of HSZ-640 catalyst (non-dealuminated protonic large pore mordenite) shows the following results: atomic ratio Si/Al of 9.80:1; a total pore volume of 0.26 ml/g; a symmetry index of 1.41; a ratio of meso plus macro porosity over the total porosity of 0.32. This catalyst is later referred as sample 42 (comparative sample).

30 g of sample 42 catalyst are added to a solution of "A" g of calcium acetate in 150 ml of water. The quantity of calcium acetate added to the solution is calculated such as to have an atomic ratio of the calcium ions in solution to the Al atoms present in the catalyst equal to "r". The mixture is heated at 80° C. and maintained at this temperature for 16 hours under vigorous stirring. The calcium exchanged mordenite is recovered by filtration, washed with demineralized water till free of excess salt, dried in air at 110° C. and then heated at 600° C. in air for 2 hours.

Table 5 lists some calcium cation exchanged non-dealuminated large pore mordenite catalysts (samples 43 to 45) prepared by the above method of example 8.

TABLE 5

Calcium cation exchanged mordenite catalysts.

| Sample | Weight of calcium acetate (A in g) | ratio r | M/Al |
|---|---|---|---|
| 43 | 3.70 | 0.50 | 0.27 |
| 44 | 7.40 | 1.00 | 0.28 |
| 45 | 14.80 | 2.00 | 0.31 |

EXAMPLE 9

Preparation of Dealuminated Large Pore Mordenite Catalyst

Sample 42 catalyst is treated with ammonium nitrate as in example 1 to exchange the remaining sodium by ammonium cations. The catalyst is dealuminated by thermal treatment carried out at 680° C. for 5 hours in the presence of steam as in example 1. After cooling the catalyst is treated at 90° C. with 6 N aqueous nitric acid under vigorous stirring for 3 hours. The catalyst is separated by filtration, washed with deionized water at 70° C., and finally dried at 150° C. for 10 hours. Analysis of the catalyst gives the following results: atomic Si/Al ratio of 110:1; a symmetry index of 1.95; a total pore volume of 0.32 ml/g; a ratio meso plus macro porosity over the total porosity of 0.37. This catalyst is later referred as sample 46 (comparative sample).

EXAMPLE 10

Preparation of Calcium Cation Exchanged Dealuminated Large Pore Mordenite Catalysts 4 g catalyst from sample 46 are added to a solution of "A" g of calcium acetate in 20 ml of water. The quantity of calcium acetate added to the solution is calculated such as to have an atomic ratio of the calcium ions in solution to the Al atoms present in the catalyst equal to "r". The mixture is heated at 80° C. and maintained at this temperature for 16 hours under vigorous stirring. The calcium exchanged mordenite is recovered by filtration, washed with demineralized water till free of excess salt, dried in air at 110° C. and then heated at 600° C. in air for 2 hours.

Table 6 lists a calcium cation exchanged dealuminated large pore mordenite catalyst (sample n° 47) prepared by the above method of example 10.

TABLE 6

Calcium cation exchanged mordenite catalyst.

| Sample | Weight of calcium acetate (A in g) | ratio r | M/Al |
|---|---|---|---|
| 47 | 0.088 | 1.00 | 0.28 |

EXAMPLE 11

Preparation of Zinc Cation Exchanged Dealuminated Small Pore Mordenite Catalyst 30 g of sample 1 catalyst are added to a solution of "A" g of zinc acetate in 150 ml of water. The quantity of zinc acetate added to the solution is calculated such as to have an atomic ratio of the zinc cations in solution to the Al atoms present in the catalyst equal to "r". The mixture is then heated at 80° C. and maintained at that temperature for 16 hours under vigorous stirring. The exchanged mordenite is recovered by filtration, washed with demineralized water till free of excess salt, dried in air at 110° C. and then heated at 600° C. for 2 hours.

Table 7 lists some zinc cation dealuminated small pore mordenite catalysts (samples 48 to 50) prepared by the above method of example 11.

TABLE 7

Zinc cation exchanged mordenite catalysts.

| Sample | Weight of zinc acetate (A in g) | ratio r | M/Al |
|---|---|---|---|
| 48 | 0.29 | 0.25 | 0.17 |
| 49 | 0.59 | 0.50 | 0.31 |
| 50 | 1.19 | 1.0 | 0.42 |

EXAMPLE 12

Preparation of Calcium Cation Exchanged Dealuminated Small Pore Mordenite Catalysts 30 g of sample 1 catalyst are added to a solution of 0.86 g of calcium acetate in 150 ml of water. The quantity of the calcium acetate added to the solution is calculated such as to have an atomic ratio of the calcium cation to the Al atoms present in the catalyst equal to 1. The mixture is heated at 80° C. and maintained at this temperature for "x" hours under vigorous stirring. The exchanged mordenite is recovered by filtration, washed with demineralized water till free of excess salt and dried in air at 110° C.; then it is optionally calcined for 2 hours at 600° C. in air.

Table 8 lists various calcium cation exchanged dealuminated small pore mordenite catalysts prepared according to example 12 with different contact times "x" and calcination times.

TABLE 8

Calcium cation exchanged dealuminated small pore mordenite catalysts.
Influence of exchange time and calcination time

| Sample | Contact time "x" | Calcination time | M/Al |
|---|---|---|---|
| 51 | 2 hours | 0 | 0.32 |
| 52 | 4 hours | 0 | 0.35 |
| 53 | 16 hours | 0 | 0.35 |
| 54 | 2 hours | 2 hours | 0.35 |
| 55 | 4 hours | 2 hours | 0.35 |

EXAMPLE 13

Preparation of Dealuminated Large Pore Mordenite Catalysts 50 g of HSZ-640 mordenite catalyst are loaded in a quartz tube placed in a furnace heated to 500° C. At 500° C. a stream of helium saturated with steam is passed at a rate of 1.5 liters/min. After 30 minutes the introduction of steam is stopped, the helium flow is lowered to 200 ml/min and the furnace is cooled to room temperature. 40 g of that steamed mordenite are then treated with 800 ml of 0.5 N hydrochloric acid at reflux for four hours under vigorous stirring. The catalyst is then separated by filtration and washed with deionized water until the filtrate has a conductivity below 20 micro Siemens /cm. The solid is then dried at 110° C. during 4 hours and calcined 12 hours at 500° C. Analysis of the catalyst gives an atomic Si/Al ratio of 23. This catalyst is later referred as sample 56. (comparative sample).

20 g of above treated catalyst as obtained after drying at 110° C. during 4 hours are added to a solution of 2.18 g of calcium acetate in 100 ml of demineralized water ("r"=1). The mixture is heated at 80° C. and maintained at this temperature for 16 hours under vigorous stirring. The exchanged mordenite is recovered by filtration, washed with demineralized water till free of excess salt, dried in air at 110° C. and then heated at 500° C. for 12 hours. Analysis shows the M/Al to be 0.28. This catalyst is later referred as sample 57.

EXAMPLE 14

Preparation of Calcium Exchanged Non-dealuminated Large Pore Mordenite Catalysts CBV 20 A mordenite catalyst (protonic large pore mordenite) has the following characteristics: atomic ratio Si/Al of 15:1; a total pore volume of 0.27 ml/g; a symmetry index of 1.09; a ratio of meso plus macro porosity over the total porosity of 0.59. This catalyst is later referred as sample 58. (comparative sample)

30 g of sample 58 catalyst are added to a solution of "A" g of calcium acetate in 150 ml of water. The quantity of calcium acetate added to the solution is calculated such as to have an atomic ratio of the calcium ions to the Al atoms present in the catalyst equal to "r". The mixture is heated at 80° C. and maintained at this temperature for 16 hours under vigorous stirring. The calcium exchanged mordenite is recovered by filtration, washed with demineralized water till free of excess salt, dried in air at 110° C. and then heated at 600° C. in air for 2 hours.

Table 9 lists calcium cation exchanged non-dealuminated large pore mordenite catalysts (samples 59 and 60) prepared by the above method of example 14.

TABLE 9

Calcium cation exchanged non-dealuminated large pore mordenite catalysts

| Sample | Weight of calcium acetate (A in g) | ratio r | M/Al |
|---|---|---|---|
| 59 | 3.4 | 0.5 | 0.2 |
| 60 | 6.8 | 1 | 0.27 |

EXAMPLE 15

Preparation of Calcium Cation Exchanged PQ Mordenite Catalysts

Mordenite provided by PQ Corporation has the following characteristics: atomic ratio Si/Al of 42:1; a total pore volume of 0.28 ml/g; a ratio of meso plus macro porosity over the total porosity of 0.49. This catalyst is later referred as sample 61. (comparative sample)

30 g of sample 61 catalyst are added to a solution of "A" g of calcium acetate in 150 ml of water. The quantity of calcium acetate added to the solution is calculated such as to have an atomic ratio of the calcium ions present in the solution to the Al atoms present in the catalyst equal to "r". The mixture is heated at 80° C. and maintained at this temperature for 16 hours under vigorous stirring. The calcium exchanged mordenite is recovered by filtration, washed with demineralized water till free of excess salt, dried in air at 110° C. and then heated at 600° C. in air for 2 hours.

Table 10 lists a catalyst (sample 62) prepared by the method of example 15.

TABLE 10

Calcium ion exchanged PQ mordenite catalyst

| Sample | Weight of calcium acetate (A in g) | ratio r | M/Al |
|---|---|---|---|
| 62 | 1.78 | 1 | 0.3 |

EXAMPLE 16

Preparation of Calcium Cation Exchanged Dealuminated Small Pore Mordenite Catalysts 20 g of sample 1 catalyst are added to a solution of "A" g of calcium acetate in 100 ml of demineralized water. The quantity of the calcium acetate added to the solution is calculated such as to have an atomic ratio of the calcium cations in solution to the Al atoms in the catalyst equal to "r". The mixture is heated at 80° C. and maintained at this temperature for 16 hours under vigorous stirring. The exchanged mordenite is recovered by filtration, washed with demineralized water till free of excess salt, dried in air at 110° C. and then heated at 600° C. in air for 2 hours.

Table 11 lists some calcium cation exchanged mordenite catalysts prepared by the method of example 16.

TABLE 11

Calcium cation exchanged dealuminated small pore mordenite catalysts

| Sample | Weight of calcium acetate (A in g) | ratio r | M/Al |
|---|---|---|---|
| 63 | 0.057 | 0.1 | 0.13 |
| 64 | 2.3 | 4 | 0.41 |

EXAMPLE 17

Calcium Species Containing Dealuminated Small Pore Mordenite Catalyst Prepared by Impregnation 10 g of sample 1 catalyst are mixed at room temperature with 15 ml of demineralized water containing 0.11 g of calcium acetate. ("r"=0.35) This slurry is stirred in a beaker for 1 hour at room temperature and dried at 110° C. for 2 hours before calcination at 600° C. for 2 hours. The amount of calcium species introduced in the catalyst corresponds to value M/Al of 0.35. This catalyst is referred as sample 65.

EXAMPLE 18

General Procedure for the Propylation of 1,1'-biphenyl Using Cation Exchanged Catalysts From Examples 2 and 3.

1,1'-biphenyl (150 g) and a catalyst selected from example 2 or 3 (7.5 g or 5% by weight of the biphenyl) are contacted with propylene at a temperature of 250° C. with an added pressure of propylene of $0.8 \times 10^5$ Pa for 5 hours in a 600ml Parr pressure autoclave operated under agitation.

The same experimental procedure is used for sample 2 to 34 catalysts, listed in Tables 1 and 2. Results of the gas chromatography analysis carried out on the reaction mixtures are given in Tables 12 and 13. Comparative results obtained with sample 1 catalyst in the same reaction conditions are indicated in both tables.

TABLE 12

Propylation of 1,1'-biphenyl with alkaline cations exchanged catalysts of example 2

| Catalyst sample | Conv. % | m,p'-Yield % | p,p'-Yield % | Di/Conv. % | p,p'-Sel. % | p-Sel. % | p,p'-/Di % |
|---|---|---|---|---|---|---|---|
| 1 (a) | 93.6 | 35.4 | 12.8 | 59.8 | 13.6 | 26.7 | 22.8 |
| 2 | 95.9 | 16.6 | 57.8 | 80.4 | 60.3 | 64.1 | 75 |
| 3 | 91.1 | 22.4 | 44.8 | 76.8 | 49.2 | 56.7 | 64 |
| 4 | 60.3 | 5.1 | 28.5 | 57.0 | 47.2 | 74.3 | 82.8 |
| 5 | 92.3 | 38.6 | 11.8 | 65.9 | 12.8 | 27.6 | 19.4 |
| 6 | 86.6 | 32.7 | 22.9 | 67.8 | 26.4 | 42.4 | 39.0 |
| 7 | 59.2 | 6.5 | 25.7 | 55.6 | 43.5 | 72.3 | 78.1 |
| 8 | 25.6 | 0.8 | 6.8 | 31.8 | 26.6 | 79.8 | 83.7 |
| 9 | 83.3 | 18.5 | 37.9 | 69.9 | 45.5 | 60.5 | 65.1 |
| 10 | 82 | 15.7 | 41.1 | 71.2 | 50.1 | 64.5 | 70.4 |
| 11 | 61.5 | 5.3 | 30.7 | 59.7 | 49.8 | 75.2 | 83.5 |
| 12 | 90.2 | 11.9 | 55.7 | 77.3 | 61.7 | 70.5 | 79.8 |
| 13 | 21.3 | 0.5 | 5.2 | 27.7 | 24.6 | 81.0 | 88.8 |
| 14 (a) | <0.2 | | | | | | |
| 15 | 71.1 | 9.6 | 36.5 | 66.3 | 51.3 | 70.7 | 77.4 |
| 16 (a) | <0.2 | | | | | | |
| 17 (a) | <0.2 | | | | | | |

(a): comparative

TABLE 13

Propylation of 1,1'-biphenyl with alkaline-earth cations exchanged catalysts of example 3

| Catalyst sample | Conv. % | m,p'-Yield % | p,p'-Yield % | Di/Conv. % | p,p'-Sel. % | p-Sel. % | p,p'-/Di % |
|---|---|---|---|---|---|---|---|
| 1 (a) | 93.6 | 35.4 | 12.8 | 59.8 | 13.6 | 26.7 | 22.8 |
| 18 | 98.0 | 42.6 | 34.7 | 83.3 | 35.4 | 37.9 | 42.5 |
| 19 | 95.4 | 32.6 | 34.2 | 73.4 | 35.8 | 47.3 | 48.8 |
| 20 | 95.8 | 21.5 | 50.1 | 78.1 | 52.3 | 58.8 | 66.9 |
| 21 | 89.3 | 36.2 | 18.0 | 64.7 | 20.1 | 39.5 | 31.0 |
| 22 | 98.0 | 16.0 | 63.1 | 84.1 | 64.3 | 67.0 | 76.5 |
| 23 | 95.6 | 12.1 | 62.9 | 81.9 | 65.8 | 74.0 | 80.3 |
| 24 | 99.2 | 20.1 | 61.1 | 85.3 | 61.5 | 70.3 | 72.2 |
| 25 | 95.4 | 15.5 | 63.0 | 83.7 | 66.0 | 70.0 | 78.9 |
| 26 | 85.0 | 8.0 | 56.5 | 78.0 | 66.5 | 75.9 | 85.2 |
| 29 | 91.3 | 36.6 | 21.5 | 67.6 | 23.5 | 40.9 | 34.8 |
| 30 | 92.2 | 29.2 | 35.1 | 71.8 | 38.0 | 52.7 | 53.0 |
| 31 | 64.3 | 5.4 | 36.1 | 65.4 | 56.2 | 89.4 | 85.8 |
| 32 | 72.8 | 19.7 | 17.3 | 52.8 | 23.7 | 55.5 | 44.9 |
| 33 | 72.3 | 8.4 | 40.5 | 68.3 | 56.1 | 74.8 | 82.1 |
| 34 | 39.5 | 1.9 | 17.3 | 48.6 | 43.7 | 82.4 | 89.7 |

(a): comparative

EXAMPLE 19

General Procedure for the Propylation of 1,1'-biphenyl with Calcium Cation Exchanged Catalysts From Examples 5,7,8 and 10

1,1'-biphenyl (150 g) and a catalyst selected from examples 5,7,8 or 10 (7.5 g or 5% by weight on the biphenyl) are contacted with propylene at a temperature of 250° C. with an added pressure of propylene of 0.8×10 power 5 Pa for 5 hours in a 600 ml Parr pressure autoclave operated under agitation. Results of gas chromatography analysis carried out on the reaction mixtures are given in Tables 14 to 17. Comparative results obtained with sample 35, 39, 42 and 46 catalysts in the same reaction conditions are indicated respectively in Tables 14,15,16 and 17.

TABLE 14

Propylation of 1,1'-biphenyl with calcium cation exchanged catalysts from example 5

| Catalyst sample | Conv. % | m,p'-Yield % | p,p'-Yield % | Di/Conv. % | p,p'-Sel. % | p-Sel. % | p,p'-/Di % |
|---|---|---|---|---|---|---|---|
| 35 (a) | 89.9 | 28.4 | 27.2 | 67.1 | 30.3 | 41.8 | 45.1 |
| 36 | 84.1 | 6.9 | 51.1 | 72.0 | 60.7 | 76.4 | 86.1 |
| 37 | 55.0 | 2.8 | 24.4 | 51.6 | 44.4 | 74.0 | 84.3 |

(a): comparative

TABLE 15

Propylation of 1,1'-biphenyl with calcium cation exchanged catalysts from example 7

| Catalyst sample | Conv. % | m,p'-Yield % | p,p'-Yield % | Di/Conv. % | p,p'-Sel. % | p-Sel. % | p,p'-/Di % |
|---|---|---|---|---|---|---|---|
| 39 (a) | 51.5 | 3.8 | 13.5 | 35.5 | 26.2 | 67.7 | 73.7 |
| 40 | 43.0 | 2.3 | 10.9 | 32.2 | 25.3 | 73.4 | 78.6 |
| 41 | 38.9 | 1.5 | 8.9 | 28.4 | 22.8 | 74.6 | 80.3 |

(a): comparative

TABLE 16

Propylation of 1,1'-biphenyl with calcium cation exchanged catalysts from example 8

| Catalyst sample | Conv. % | m,p'-Yield % | p,p'-Yield % | Di/Conv. % | p,p'-Sel. % | p-Sel. % | p,p'-/Di % |
|---|---|---|---|---|---|---|---|
| 42 (a) | 89.9 | 22.1 | 19.9 | 54.7 | 22.2 | 43.5 | 40.6 |
| 44 | 97.4 | 1.5 | 44.2 | 71.1 | 45.4 | 52.8 | 63.8 |
| 45 | 71.9 | 7.6 | 22.2 | 45.1 | 30.9 | 64.2 | 68.6 |

(a): comparative

TABLE 17

Propylation of 1,1'-biphenyl with calcium cation exchanged catalysts from example 10

| Catalyst sample | Conv. % | m,p'-Yield % | p,p'-Yield % | Di/Conv. % | p,p'-Sel. % | p-Sel. % | p,p'-/Di % |
|---|---|---|---|---|---|---|---|
| 46 (a) | 73.6 | 5.3 | 42.2 | 65.6 | 57.3 | 78.3 | 87.4 |
| 47 | 74.2 | 6.2 | 42.3 | 66.5 | 56.9 | 76.6 | 85.7 |

(a): comparative

EXAMPLE 20

Propylation of Diphenyl Ether with Calcium Cation Exchanged Sample 26 Catalyst

Diphenyl ether (150 g) and 7.5 9 of catalyst of sample 26 (5% by weight on the diphenyl ether) are contacted with propylene at a temperature of 250° C. with an added pressure of propylene of 0.8×10 power 5 Pa for 5 hours in a 600 ml Parr pressure autoclave operated under agitation. Results of the gas chromatography analysis carried out on the reaction mixture are given in Table 18. Comparative results obtained with sample 1 catalyst in the same reaction conditions are also indicated.

EXAMPLE 21

Propylation of Para-terphenyl with Calcium Cation Exchanged Sample 26 Catalyst

Para-terphenyl (150 g) and 7.5 g of catalyst 26 (5% by weight on the p-terphenyl) are contacted with propylene at a temperature of 250° C. with an added pressure of propylene of 0.8×10 power 5 Pa for 5 hours in a 600 ml Parr pressure autoclave operated under agitation. Results of the gas chromatography analysis carried out on the reaction mixture are given in Table 19. Comparative results obtained with sample 1 catalyst in the same reaction conditions are also indicated.

EXAMPLE 22

Propylation of Naphthalene with Calcium Cation Exchanged Sample 24 and 26 Catalysts Naphthalene (150 g) and 7.5 g of sample 24 or 26 catalysts (5% by weight of the naphthalene) are contacted with propylene at a temperature of 250° C. with an added pressure of propylene of 0.8×10 power 5 Pa for 5 hours in a 600 ml Parr pressure autoclave operated under agitation. Results of the gas chromatography analysis carried out on the reaction mixtures are given in Table 20. Comparative results obtained with sample 1 catalyst in the same reaction conditions are also indicated.

TABLE 18

Propylation of diphenyl ether with calcium cation exchanged sample 26 catalyst

| Catalyst sample | Conv. % | m,p'-Yield % | p,p'-Yield % | Di/Conv. % | p,p'-Sel. % | p-Sel. % | p,p'-/Di % |
|---|---|---|---|---|---|---|---|
| 1 (a) | 92.4 | 36.0 | 27.5 | 74.8 | 29.7 | 45.8 | 39.7 |
| 26 | 80.4 | 11.1 | 44.3 | 71.4 | 55.1 | 78.5 | 77.2 |

(a): comparative

TABLE 19

Propylation of para-terphenyl with calcium cation exchanged sample 26 catalyst

| Catalyst sample | Conv. % | m,p"-Yield % | p,p"-Yield % | Di/Conv. % | p,p"-Sel. % | p-Sel. % | p,p"-/Di % |
|---|---|---|---|---|---|---|---|
| 1 (a) | 77.9 | 7.9 | 37.5 | 58.2 | 48.2 | 77.1 | 82.7 |
| 26 | 58.1 | 2.3 | 28.2 | 52.9 | 48.5 | 89.2 | 91.6 |

(a): comparative

TABLE 20

Propylation of naphthalene with calcium cation exchanged samples 24 and and 26 catalysts

| Catalyst sample | Conv. % | 2,7-Yield % | 2,6-Yield % | Di/Conv. % | 2,6-Sel. % | 2-Sel. % | 2,6-/Di % |
|---|---|---|---|---|---|---|---|
| 1 (a) | 82.3 | 15.0 | 9.4 | 32.5 | 11.5 | 75.9 | 35.3 |
| 24 | 96.6 | 13.6 | 54.2 | 71.6 | 56.1 | 83.7 | 78.3 |
| 26 | 22.3 | 0.8 | 3.2 | 18.0 | 14.4 | 96.1 | 80 |

(a): comparative

TABLE 21

Propylation of 1,1'-biphenyl with zinc cation exchanged catalysts from example 11

| Catalyst sample | Conv. % | m,p'-Yield % | p,p'-Yield % | Di/Conv. % | p,p'-Sel. % | p-Sel. % | p,p'-/Di % |
|---|---|---|---|---|---|---|---|
| 1 (a) | 93.6 | 35.4 | 12.8 | 59.8 | 13.6 | 26.7 | 22.8 |
| 48 | 85 | 29.1 | 23.1 | 64.3 | 27.2 | 47.6 | 42.3 |
| 49 | 98.6 | 17.8 | 62.9 | 84.5 | 63.8 | 65.9 | 75.5 |
| 50 | 97.1 | 16.0 | 61.4 | 83.8 | 63.3 | 66.8 | 75.5 |

(a): comparative

EXAMPLE 23

Propylation of 1,1'-biphenyl Using Zinc Cation Exchanged Catalysts From Example 11

1,1'-biphenyl (150 g) and a zinc cation exchanged catalyst selected from example 11 (7.5 g or 5% by weight on the biphenyl) are contacted with propylene at a temperature of 250° C. with an added pressure of propylene of 0.8×10 power 5 Pa for 5 hours in a 600 ml Parr pressure autoclave operated under agitation. Results of the gas chromatography analysis carried out on the reaction mixtures are given in Table 21. Comparative results obtained with sample 1 catalyst in the same reaction conditions are also indicated.

EXAMPLE 24

Propylation of 1,1'-biphenyl Using Calcium Cation Exchanged Catalysts From Example 14

1,1'-biphenyl (150 g) and a calcium cation exchanged cation catalyst selected from example 14 (7.5 g or 5% by weight on the biphenyl) are contacted with propylene at a temperature of 250° C. with an added pressure of propylene of 0.8×10 power 5 Pa for 5 hours in a 600 ml Parr pressure autoclave operated under agitation. Results of the gas chromatography analysis carried out on the reaction mixtures are given in Table 22. Comparative results obtained with sample 58 in the same conditions are indicated.

EXAMPLE 25

Propylation of 1,1'-biphenyl Using the Calcium Exchanged Catalyst from Example 15

1,1'-biphenyl (150 g) and the calcium cation exchanged catalyst from example 15 (7.5 g or 5% by weight on the biphenyl) are contacted with propylene at a temperature of 250° C. with an added pressure of propylene of 0.8×10 power 5 Pa for 5 hours in a 600 ml Parr pressure autoclave operated under agitation. Results of the gas chromatography analysis carried out on the reaction mixtures are given on Table 23. Comparative results obtained with sample 61 catalyst in the same reaction conditions are also indicated.

EXAMPLE 26

Propylation of 1,1'-biphenyl Using Calcium Cation Exchanged Catalysts From Example 12

1,1'-biphenyl (150 g) and a calcium cation exchanged catalyst selected from example 12 (7.5 g or 5% by weight on the biphenyl) are contacted with propylene at a temperature of 250° C. with an added pressure of propylene of 0.8×10 power 5 Pa for 5 hours in a 600 ml Parr pressure autoclave operated under agitation. Results of the gas chromatography analysis carried out on the reaction mixtures are given in Table 24.

TABLE 22

Propylation of 1,1'-biphenyl with calcium cation exchanged catalysts from example 14

| Catalyst sample | Conv. % | m,p'-Yield % | p,p'-Yield % | Di/Conv. % | p,p'-Sel. % | p-Sel. % | p,p'-/Di % |
|---|---|---|---|---|---|---|---|
| 58 (a) | 86.5 | 20.2 | 6.8 | 46.5 | 23.4 | 25.0 | 16.8 |
| 59 | 92.2 | 20.4 | 35.2 | 64.5 | 38.2 | 51.9 | 59.1 |
| 60 | 39.7 | 1.4 | 8.4 | 27.2 | 21.2 | 71.0 | 77.9 |

(a): comparative

TABLE 23

Propylation of 1,1'-biphenyl with the calcium cation exchanged catalyst from example 15

| Catalyst sample | Conv. % | m,p'-Yield % | p,p'-Yield % | Di/Conv. % | p,p'-Sel. % | p-Sel. % | p,p'-/Di % |
|---|---|---|---|---|---|---|---|
| 61 (a) | 90.0 | 35.1 | 20.2 | 68.7 | 22.5 | 32.8 | 32.7 |
| 62 | 69.5 | 6.7 | 37.4 | 65.1 | 53.8 | 74.4 | 82.6 |

(a): comparative

TABLE 24

Propylation of 1,1'-biphenyl with calcium cation exchanged catalysts from example 12

| Catalyst sample | Conv. % | m,p'-Yield % | p,p-'Yield % | Di/Conv. % | p,p'-Sel. % | p-Sel. % | p,p'-/Di % |
|---|---|---|---|---|---|---|---|
| 51 | 78.2 | 8.3  | 45.3 | 69.6 | 57.9 | 75.8 | 83.1 |
| 52 | 77.7 | 6.6  | 48.0 | 71.5 | 61.8 | 78.2 | 86.4 |
| 53 | 76.2 | 6.2  | 47.4 | 71.4 | 62.3 | 78.4 | 87.1 |
| 54 | 83.6 | 12.9 | 48.4 | 74.6 | 57.9 | 70.5 | 77.5 |
| 55 | 92.5 | 14.2 | 60.2 | 82.0 | 65.1 | 71.7 | 79.4 |

TABLE 25

Propylation of 1,1'-biphenyl with the calcium cation exchanged catalyst from example 13

| Catalyst sample | Conv. % | m,p'-Yield % | p,p-'Yield % | Di/Conv. % | p,p'-Sel. % | p-Sel. % | p,p'-/Di % |
|---|---|---|---|---|---|---|---|
| 56 (a) | 93.6 | 28.3 | 26.1 | 64.5 | 27.9 | 38.4 | 43.2 |
| 57     | 73.2 | 8.5  | 29.7 | 54.1 | 40.5 | 68.4 | 74.9 |

(a): comparative

EXAMPLE 27

Propylation of 1,1'-biphenyl Using the Calcium Cation Exchanged Catalyst From Example 13

1,1'-biphenyl (150 g) and the calcium cation exchanged catalyst from example 13 (7.5 g or 5% by weight on the biphenyl) are contacted with propylene at a temperature of 250° C. with an added pressure of propylene of 0.8×10 power 5 Pa for 5 hours in a 600 ml Parr pressure autoclave operated under agitation. Results of the gas chromatography analysis carried out on the reaction mixtures are given in Table 25. Comparative results obtained with sample 56 catalyst in the same reaction conditions are also indicated.

EXAMPLE 28

Propylation of 1,1'-biphenyl Using Calcium Cation Exchanged Catalysts From Example 16

1,1'-biphenyl (150 g) and a calcium exchanged catalyst selected from example 16 (7.5 g or 5% by weight on the biphenyl) are contacted with propylene at a temperature of 250° C. with an added pressure of propylene of 0.8×10 power 5 Pa for 5 hours in a 600 ml Parr pressure autoclave operated under agitation. Results of the gas chromatography analysis carried out on the reaction mixtures are given in Table 26. Comparative results obtained with sample 1 catalyst in the same reaction conditions are also indicated.

EXAMPLE 29

Propylation of 1,1'-biphenyl Using the Calcium Species Containing Catalyst From Example 17

1,1'-biphenyl (150 g) and the calcium species containing catalyst from example 17 (sample 65) (7.5 g or 5% by weight on the biphenyl) are contacted with propylene at a temperature of 250° C. with an added pressure of propylene of 0.8×10 power 5 Pa for 5 hours in a 600 ml Parr pressure autoclave operated under agitation. Results of the gas chromatography analysis carried out on the reaction mixtures are given in Table 27. Comparative results obtained with sample 1 catalyst in the same reaction conditions are also indicated.

TABLE 26

Propylation of 1,1'-biphenyl with calcium cation exchanged catalysts from example 16

| Catalyst sample | Conv. % | m,p'-Yield % | p,p-'Yield % | Di/Conv. % | p,p'-Sel. % | p-Sel. % | p,p'-/Di % |
|---|---|---|---|---|---|---|---|
| 1 (a) | 93.6 | 35.4 | 12.8 | 59.8 | 13.6 | 26.7 | 22.8 |
| 63    | 96.3 | 44.6 | 17.6 | 74.7 | 18.3 | 27.0 | 24.5 |
| 64    | 17.4 | 0.4  | 4.0  | 26.0 | 22.8 | 83.3 | 87.6 |

(a): comparative

TABLE 27

Propylation of 1,1'-biphenyl with the calcium species containing exchanged catalyst from example 17

| Catalyst sample | Conv. % | m,p'-Yield % | p,p'-Yield % | Di/Conv. % | p,p'-Sel. % | p-Sel. % | p,p'-/Di % |
|---|---|---|---|---|---|---|---|
| 1 (a) | 93.6 | 35.4 | 12.8 | 59.8 | 13.6 | 26.7 | 22.8 |
| 65 | 56.9 | 5.9 | 25.4 | 55.9 | 44.8 | 83.3 | 80.0 |

(a): comparative

We claim:

1. A process for the selective alkylation of a polycyclic aromatic derivative yielding improved conversion and increased alkylation selectivity towards para-positions, said process comprising:

reacting the polycyclic aromatic derivative with an alkylating agent in the presence of a catalyst, wherein said catalyst being a protonic form of a mordenite having an atomic Si/Al ratio of at least 5:1 and having a biphenyl sorption of at least 0.05 g biphenyl per g of catalyst, said protonic mordenite catalyst is the product of the steps of (a) replacing sodium in a large pore or small pore mordenite material with proton or ammonium to form an exchanged mordenite, (b) dealuminating said exchanged mordenite, effective to remove aluminum from the exchanged mordenite crystal network, to form a dealuminated mordenite, and (c) adding an additional metal species to said dealuminated mordenite to form said protonic mordenite catalyst containing said additional metal species in a molar ratio metal (in the metal species)/aluminum of at least 0.10.

2. The process of claim 1 wherein the mordenite is a large pore mordenite.

3. The process of claim 2 wherein the mordenite has an atomic Si/Al ratio between 30:1 and 200:1.

4. The process of claim 3 wherein the mordenite has an atomic Si/Al ratio between 60:1 and 150:1.

5. The process of claim 1 wherein the mordenite is a small pore mordenite.

6. The process of claim 5 wherein mordenite has an atomic Si/Al ratio between 30:1 and 200:1.

7. The process of claim 5 or 6 wherein mordenite has an atomic Si/Al ratio between 60:1 and 150:1.

8. The process of claim 1 wherein the mordenite catalyst comprises metal species in a molar ratio metal (in the metal species)/aluminum between 0.10 and 0.85.

9. The process of claim 8 wherein the metal in the metal species is an alkali metal, an alkaline-earth metal or a metal of group 12, or any mixture thereof.

10. The process of claim 9 wherein metal species are lithium cations, calcium cations, magnesium cations or zinc cations.

11. The process of claim 8 wherein the metal species have been introduced in the mordenite via cation exchange or impregnation or a combination thereof.

12. The process of claim 8 wherein the step of replacing the sodium is carried out via a treatment with an inorganic or organic acid or aqueous solution thereof.

13. The process of claim 8 wherein the dealumination step is carried out by one or more combined hydrothermal and acid treatments, and wherein the additional metal species is added by a cation exchange step carried out by treatment of the dealuminated mordenite with an aqueous solution of a selected ionizable metal salt or mixture of metal salts, and which is followed by a drying step and optionally also by a calcination step carried out at a temperature between 300° C. and 900° C.

14. The process of claim 8 wherein the polycyclic aromatic derivative is a derivative of formula (I) $Ar^1$ (—X—$Ar^2)_n$—$Ar^3$
wherein $Ar^1$ may represent a non-substituted or substituted phenyl group or a non-substituted or substituted fused or non-fused polycyclic aromatic hydrocarbon group;

$Ar^2$ may represent a non-substituted or substituted phenyl group;

$Ar^3$ may represent a hydrogen atom or a non-substituted or substituted phenyl group;

X may be absent or represent an oxygen atom, a sulphur atom, a carbonyl group, a sulfonyl group or a $C_1$–$C_4$ alkylene group; n may be zero, one or two, provided that, when n is zero and $Ar^1$ is a phenyl group, then $Ar^3$ is different from hydrogen; and wherein the phenyl groups in $Ar^1$, $Ar^2$ and $Ar^3$ and the fused or non-fused polycyclic aromatic hydrocarbon group in $Ar^1$ may be substituted, independently from each other, by one or more substituents selected from a halogen, a hydroxy group, a $C_1$–$C_6$ alkoxy group, a $C_1$–$C_4$ alkoxycarbonyl group, or a $C_1$–$C_{20}$ alkyl group which itself may be substituted by a halogen, a hydroxy, a $C_1$–$C_4$ alkoxy, a carboxy or a $C_1$–$C_4$ alkoxycarbonyl radical; provided that, if $Ar^1$ and/or $Ar^3$ represent a phenyl group, or if $Ar^1$ represents a non-fused polycyclic aromatic hydrocarbon, then at least one para-position is unsubstituted, and if $Ar^1$ represents a fused polycyclic aromatic hydrocarbon group, then at least one beta-position is unsubstituted.

15. The process of claim 14 wherein the polycyclic aromatic derivative is a derivative of formula $Ar^1$ (—X—$Ar^2)_n$—$Ar^3$ (I)
wherein:

$Ar^1$ represents a non-substituted or substituted phenyl group or a non-substituted or substituted 1,1'-biphenyl group, a para-terphenyl group, a naphthyl group, a fluorenyl group or an anthracenyl group, $Ar^2$ represents a non-substituted or substituted phenyl group, $Ar^3$ represents a hydrogen atom or a non-substituted phenyl group, X may be absent or represent an oxygen atom, a sulphur atom, a carbonyl group, a sulfonyl group or a $C_1$–$C_4$ alkylene group, n may be zero, one or two, provided that when n is zero and $Ar^1$ is a phenyl group, then $Ar^3$ is different from hydrogen.

16. The process of claim 15 wherein the polycyclic aromatic derivative is 1,1'-biphenyl, or p-terphenyl, or naphthalene, or diphenyl ether or 1,4-diphenoxybenzene.

17. The process of claim 8 wherein the alkylating agent is a $C_2$–$C_{20}$ alkene, a $C_2$–$C_{20}$ polyolefin, a $C_4$–$C_7$ cycloalkene, a $C_1$–$C_{20}$ alkanol, a $C_1$–$C_{20}$ alkyl halide or a $C_1$–$C_{20}$ alkyl (monocyclic or polycyclic) aromatic hydrocarbon derivative.

18. The process of claim 17 wherein the alkyating agent is a $C_1$–$C_4$ alkene or a $C_1$–$C_4$ alkyl halide or a $C_1$–$C_4$ alkanol.

19. The process of claim 18 wherein the alkylating agent is propene.

20. The process of claim 6 wherein the mordenite catalyst comprises metal species in a molar ratio metal (in the metal species)/aluminum between 0.20 and 0.70.

* * * * *

UNITED STATES PATENT AND TRADEMARK OFFICE
CERTIFICATE OF CORRECTION

PATENT NO. : 5,900,519
DATED : May 4, 1999
INVENTOR(S) : Notte, et al.

It is certified that error appears in the above-identified patent and that said Letters Patent are hereby corrected as shown below:

Column 35, line 7, please replace the phrase, "C1-C4 alkene" with "C3-C4 alkene".

Column 19, line 11, please delete the term, "R-839".

Column 19, line 16, please replace the word "Cealuminated" with the word "Dealuminated".

Column 27, line 17, please replace "7.5 9" with "7.5 g".

Signed and Sealed this

Eighth Day of May, 2001

*Attest:*

NICHOLAS P. GODICI

*Attesting Officer*      *Acting Director of the United States Patent and Trademark Office*